US012616609B2

(12) United States Patent
Bischoff et al.

(10) Patent No.: US 12,616,609 B2
(45) Date of Patent: May 5, 2026

---

(54) EQUIPMENT AND METHODS FOR REFRACTIVE SURGERY, PARTICULARLY FOR KERATOPLASTY

(71) Applicant: Carl Zeiss Meditec AG, Jena (DE)

(72) Inventors: Mark Bischoff, Jena (DE); Robert Pomraenke, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 619 days.

(21) Appl. No.: 17/995,216

(22) PCT Filed: Mar. 26, 2021

(86) PCT No.: PCT/EP2021/058022
§ 371 (c)(1),
(2) Date: Sep. 30, 2022

(87) PCT Pub. No.: WO2021/198106
PCT Pub. Date: Oct. 7, 2021

(65) Prior Publication Data
US 2023/0218443 A1 Jul. 13, 2023

(30) Foreign Application Priority Data

Apr. 1, 2020 (DE) .......................... 102020204261.6

(51) Int. Cl.
*A61F 9/008* (2006.01)
*A61F 2/14* (2006.01)

(52) U.S. Cl.
CPC .......... *A61F 9/00831* (2013.01); *A61F 2/142* (2013.01); *A61F 2009/00853* (2013.01);
(Continued)

(58) Field of Classification Search
CPC ................. A61F 9/00831; A61F 2/142; A61F 2009/00853; A61F 2009/00855;
(Continued)

(56) References Cited

U.S. PATENT DOCUMENTS

2003/0014042 A1 1/2003 Juhasz et al.
2004/0236392 A1 11/2004 Dick et al.
(Continued)

FOREIGN PATENT DOCUMENTS

DE 102007019815 10/2008
RU 2652753 4/2018
(Continued)

OTHER PUBLICATIONS

International Search Report (English translation) and Written Opinion for PCT/EP2021/058022 dated mailed Jun. 25, 2021.
(Continued)

*Primary Examiner* — Carl H Layno
*Assistant Examiner* — Aya Ziad Bakkar
(74) *Attorney, Agent, or Firm* — DeWitt LLP

(57) ABSTRACT

Equipment and methods for refractive surgery, including for keratoplasty. The invention describes equipment and methods for the production and implantation of a lamella of a tissue or material for the purpose of correcting a corneal geometry at maximum precision that is thus improved in relation to the prior art. The invention facilitates restoration of normal corneal geometry together with optical functionality of the cornea which is improved in relation to the prior art. A planning device, a treatment system and a planning method are designed to couple a device coordinate systems of the laser devices involved and characterization devices by application of registration and to uniquely register the supplied measurement data for generating the lamella to be implanted to the device coordinate systems by a specific, defined edge geometry of a blank from which the lamella is produced, and by the lamella, and by additional system and method aids.

20 Claims, 6 Drawing Sheets

(52) U.S. Cl.
CPC .............. *A61F 2009/00855* (2013.01); *A61F*
*2009/00872* (2013.01); *A61F 2009/00882*
(2013.01); *A61F 2240/004* (2013.01)

(58) Field of Classification Search
CPC .. A61F 2009/00872; A61F 2009/00882; A61F
2240/004
See application file for complete search history.

(56) References Cited

U.S. PATENT DOCUMENTS

| | | | | |
|---|---|---|---|---|
| 2009/0247999 | A1* | 10/2009 | Tuan | .................. A61F 9/00831 |
| | | | | 606/5 |
| 2014/0264980 | A1 | 9/2014 | Muller | |
| 2017/0027754 | A1 | 2/2017 | Muller | |
| 2017/0319329 | A1* | 11/2017 | Muller | ................... A61F 2/142 |

FOREIGN PATENT DOCUMENTS

| | | |
|---|---|---|
| WO | WO0189373 | 11/2001 |
| WO | WO2006128038 | 11/2006 |
| WO | WO2008131888 | 11/2008 |
| WO | WO2020212199 | 10/2020 |

OTHER PUBLICATIONS

Homolka et al., "Das Excimer Laser Corneal Shaping—(ELCS) System: Hochpräzise Herstellung von Hornhaut-(Corena-) Transplantaten mittels Excimer Laser-Ablation", Bol. 117 (2000).

* cited by examiner

EQUIPMENT AND METHODS FOR REFRACTIVE SURGERY, PARTICULARLY FOR KERATOPLASTY

RELATED APPLICATIONS

This application is a National Phase entry of PCT Application No. PCT/EP2021/058022 filed Mar. 26, 2021, which application claims the benefit of priority to DE Application No. 10 2020 204 261.6, filed Apr. 1, 2020, the entire disclosures of which are incorporated herein by reference.

TECHNICAL FIELD

The present invention relates to apparatuses and methods of refractive surgery, in particular for keratoplasty, for example sutureless intrastromal anterior lamellar keratoplasty (sIALK).

BACKGROUND

Apparatuses and methods of refractive surgery, in particular for keratoplasty, for example as described in DE 10 2007 019 815 A1 and WO 2008/131888 A1, have previously assumed that a piece of tissue is always taken from the recipient's eye during the treatment. To this end, the sIALK method has hitherto been described in such a way that there always has to be a resection because only this creates a depression in the stromal bed (vacancy) which simplifies an implementation of an implant or transplant in the correct position. A vacancy has inherent disadvantages, for example the burden of surgery connected to the generation and the loss of tissue. However, the advantages often dominate: obtaining biopsy material and simplified positioning of the implant.

In a certain configuration, there is also an improvement in the uncorrected visual acuity (UDVA) in addition to an improvement in the corrected visual acuity (CDVA). Thus, the visual acuity is corrected at the same time. In parts, this idea has also already been formulated in DE 10 2007 019 815 A1 or WO 2008/131888 A1.

Shaping can be implemented in different ways within the scope of the production of the implant, more particularly a tissue implant. One possible procedure consists of impressing the target geometry on an implant blank by application of laser processing. For refractive surgery, in particular, this is a procedure of interest because the refractive laser systems conventional there can be adapted to such methods with little outlay. Consequently, the patient-specific adaptation of the implant could be carried out by the medical user in the clinic and would not have to be implemented in a tissue bank or elsewhere. Thus, such an approach would have logistical advantages and would also reduce some risks to the patients.

However, the required processing accuracy cannot be reliably obtained in the case of a simple transfer of a PRK or LASIK treatment procedure to the problem of the implant production. This is down to the fact that in contrast to the usual use when shaping stromal corneal tissue for the subtractive correction of a refractive error, in which tissue layers up to approximately 13 µm thick are removed per diopter correction and hence there hardly ever is a maximum removal of more than 100 µm, a removal of more than 100 µm layer thickness is not unusual during the implant production. To ultimately obtain an absolute accuracy of the order of micrometers when removing so much is more difficult than to obtain the high relative requirement in terms of accuracy during a PRK correction, especially since the properties of the implant material may be subject to greater variations than is the case for stromal tissue during a PRK or LASIK treatment.

Particularly high accuracy is required when shaping the implant within the correction zone of the tissue, which may be a natural donor corneal tissue or an artificial tissue with identical properties to natural corneal tissue, and for the geometry of the edge of said implant. Accurate fitting into an available vacancy in the tissue is often required for the periphery of the implant, which is referred to as an edge. (An accuracy of at least 10 µm, and 5 µm or less where possible, should be obtained in this case. In the ideal case, fitting can be implemented with 1 µm accuracy.) One aspect of this problem consists of the fact that the surgeon may not damage the edge of the implant during the entire process, for example when separating the tissue to be transplanted from the surrounding tissue of the donor eye or when separating unneeded parts from the material. Naturally, these process steps require manual microsurgical work using surgical instruments.

SUMMARY OF THE INVENTION

Example embodiments of the invention include apparatuses and methods for producing and implanting a lamella of a tissue or material for the purposes of correcting a corneal geometry with the greatest precision, and hence with a better precision than in the prior art. In particular, embodiments of the invention assist in restoring a normal corneal geometry with a better optical function of the cornea than in the prior art.

The invention includes various measures or features which all serve the purpose of improving the aforementioned apparatuses and methods of refractive surgery, in particular for keratoplasty, and which are ultimately used to achieve the production and implantation of a tissue or material for the purposes of correcting a corneal geometry with a better precision than in the prior art.

The optimized target geometry sought after by the apparatuses and methods according to the invention described here is intended to improve the optical function of the cornea, and an approximately normal corneal geometry should be generated or restored at the same time.

The measures or features are intended to lead to an improved shape of the implant (for the purposes of avoiding cavities) and to an improved processing accuracy. optimally prepare the periphery of the (natural or artificial) tissue or material for the manual method steps and/or to simplify or else, where possible, replace critical method steps by laser processing, and also to describe measures for the purposes of improving the accuracy of the laser processing and reducing the load on or damage to the implant.

However, a few terms should be clarified before these groups are described in detail:

"Implant" is a tissue, in particular an (optionally modified) corneal tissue of a donor eye or an artificial tissue or material of non-human origin with identical properties.

"Transplant" is a tissue of human origin. (The distinction on the basis of contained living cells may be relevant from a regulatory point of view but is neglected here.)

"Implantation" refers to the insertion both of an implant and of a transplant.

"Blank" refers to a workpiece. This workpiece may be an implant or transplant which generally has a three-dimensionally curved, round basic shape with a diameter of approximately 5-9 mm and a thickness ranging between 10 µm and 400 µm, at most 500 µm. The thickness profile of this spherical shell or this spherical shell-like structure with a radius of curvature between 5 mm and infinity has not yet been fitted to the recipient's eye. A lamella is created from the blank by processing.

"Lamella" refers to an implant or transplant which is generated from a blank and which obtains a thickness profile specifically fitted to the recipient's eye. Consequently, the lamella is the finished product ready for insertion into a cut surface in the cornea of a recipient's eye or into a vacancy (structure) defined by this cut surface, the cut surface having been prepared to this end.

"Vacancy" denotes the structure in the stromal bed that arises from the resection (i.e., the removal of a corneal volume). The vacancy may also be referred to as resection cavity even though it practically never really exists as a cavity in the cornea; instead, the lamella situated thereabove always largely comes into contact with the stromal bed and an initially created cavity is quickly filled with tissue fluid.

Example embodiments of the invention include a planning device according to the invention for generating control data for a treatment system for refractive surgery, in particular for keratoplasty, said treatment system comprising a first laser device and at least one characterization device, with the first laser device, for example a femtosecond laser device, being rendered controllable by application of the control data so as to generate at least one cut surface in a cornea of an eye. On account of the tasks that this first laser device has to fulfill, it is necessary for a processing laser beam emitted thereby to be able to penetrate into an eye tissue, in particular into the cornea of an eye, and to be able to generate a cut surface within the tissue. Laser devices where a focus of the processing laser beam thereof in the tissue is able to generate photodisruption of the tissue are usually suitable to this end.

The planning device furthermore comprises:

an interface for supplying first measurement data regarding parameters of the cornea to the characterization device, for example an OCT (optical coherence tomography) device, an interface for supplying second measurement data or model data about a lamella which is able to be inserted into the cornea following the generation of the cut surface, an interface for transmitting control data to the first laser device, and calculation structure for defining the at least one cut surface in the cornea using the first measurement data and the second measurement data or model data, the calculation structure generating a control data set for controlling the first laser device and the at least one cut surface being generable by the first laser device using the control data record.

The at least one cut surface to be generated in the cornea of an eye, of the recipient's eye, can be simple in this case and can really have only one generally curved surface, into which the lamella can be "pushed in". However, this may also outline a volume—made by a plurality of cut surfaces—which can be removed in order to subsequently introduce the lamella into the vacancy that has arisen in this case.

The planning device is furthermore configured to generate control data for a second laser device of the treatment system, for example an excimer laser device, for the purposes of processing a blank to form the lamella shaped in patient-specific fashion, and comprises an interface for transmitting control data to the second laser device, with the first laser device, the second laser device and the characterization device each having an equipment coordinate system and these devices being coupled or couplable with respect to one another by use of a registration of the equipment coordinate systems, and the supplied second measurement data or model data of the lamella being registrable with respect to these equipment coordinate systems. On account of the tasks that this second laser device has to fulfill, it is necessary for a processing laser beam emitted thereby to be able to ablate eye tissue, in particular ablate the cornea of an eye from its surface into the tissue. Even though—naturally—work can also be carried out here using a processing laser beam that generates photodisruption in the tissue, laser devices whose processing laser beam can process the tissue by application of ablation are particularly suitable to this end.

The blank is likewise processed, for example by application of an excimer laser device, in such a way that the processing profile of the laser device (fluence or laser shot distribution as a function of location) is "placed" exactly on the blank; normally, this requires a centration with an accuracy of approximately 100 µm. As a result, the blank is formed into the patient-specific lamella, the implantation of which brings about the intended regularization of the pachymetry and optionally a refraction adaptation.

Holistic planning of the operation is very important. To this end, the planning device carries out a planning method which is encoded in planning software in the planning device. To this end, the measured corneal tomography data and optionally further biometry parameters (e.g., radius of curvature, refraction) of the eye to be treated are used as input for the planning software. To this end, the planning device in which the planning software is encoded can be an integrative constituent part of the treatment system or else be localized in parallel or alternatively on one or more computers spatially separated from the treatment system.

In this case, the spatially resolved pachymetry of the patient is indicated to the user, as well as at least one further position marking (e.g., center of the photopic pupil or corneal sight center, vertex position, limbus). Moreover, the software comprises the information of the typical pachymetry map of a healthy eye. The software automatically determines a difference map by way of forming a positionally correct difference between the existing pachymetry map and a typical pachymetry map. The user decides whether the method should be carried out with or without vacancy, defines the treatment zone (generally round) by virtue of for example defining lamella center and lamella diameter, and defines further geometry parameters, for example diameter and edge thickness of the vacancy, edge thickness of the lamella, depth of the pocket cut below the corneal surface. The surface can also automatically propose or define some or all of these parameters. Then, the software generates both control data for the first laser device, that is to say for example a femtosecond laser device, and control data for the second laser device, for example the excimer laser device.

Depending on the state of the blank from which the patient-specific lamella should be constructed, it is optionally very advantageous for example if the planning device according to the invention is furthermore configured to generate control data for the first laser device or a further laser device, likewise for example a femtosecond laser device, the equipment coordinate system of which is likewise coupled to the aforementioned equipment coordinate systems by use of a registration, in order to generate or pre-process the blank, with the blank being able to be generated from a natural donor cornea or from artificial tissue, or the blank being pre-processable therein, by generating one or more cut surfaces in the donor cornea or the artificial tissue by application of the first laser device or the further laser device.

To this end, the control data can and should contain registration information, in particular:

1. The control data for, e.g., a femtosecond laser device as pre-processing further laser device for generating a blank in an initial material, optionally in the cornea of a donor eye or in an artificial tissue. Should the initial material already be available in a suitable configuration, this step can be replaced by feeding data about the geometry of the material.

2. The control data for, e.g., an excimer laser device as post-processing second laser device for processing the blank to form the lamella.

3. The control data for generating at least one cut surface, that is to say for example a pocket cut or a vacancy in the recipient's eye for accommodating the lamella, for, e.g., a femtosecond laser device as first laser device.

An example embodiment of the planning device according to the invention is configured to generate control data for a temperature regime for maintaining a temperature below a maximum temperature for processing the blank to form the lamella using the second laser device. Processing the blank to form the lamella by application of ablation by way of this second laser device generally leads to the tissue to be processed heating up on account of the high energy input. However, to be able to ensure precise structuring, the processing temperature of the tissue should not vary, and it is better to keep the latter constant at a low temperature.

In a variant of the invention, the blank is actively cooled before and/or during the processing with the second laser device, which is usually an excimer laser device. In a specific variant of the invention, the cooling is to below 10° C. In another variant of the invention, the cooling is to below the freezing point of the blank. The waste products of the processing are actively removed by operation of a controlled air stream. In a variant of the invention, the air flow is actively controlled in respect of temperature and/or humidity. In a variant of the invention, the cooling is down to the dew point of the air in the air flow. In another variant of the invention, an industrial gas (e.g., nitrogen) is used in place of air. In a further variant of the invention, the processing is monitored continuously or cyclically. By way of example, monitored parameters include the surface temperature, ablated volume, material thickness, surface topography, axial position of the blank and lateral position of the blank. The monitored parameters are used to control the ablation process in a configuration of the invention.

An important consideration when planning (and subsequently carrying out) the generation of a patient-specific lamella with very high precision relates to the provision of different zones in the blank and the subsequent lamella.

Therefore, it is very advantageous for example if the planning device is configured to determine a substantially ring-shaped transition zone at the edge of the lamella, within which the edge thickness gradually transitions to a patient-specific thickness profile, and furthermore control data are generated such that there is no processing of the edge of the lamella by the second laser device, with the second laser device for processing the blank to form the patient-specifically shaped lamella comprising a holder on which the blank is affixable during the treatment by the second laser device.

When using a holder for processing the blank by application of the second laser device, the planning device in an embodiment is configured to generate control data for active cooling of the holder.

Should the blank not yet have the dimensions suitable for processing by application of the second laser device, the planning device in a first example variant is configured to define cut surfaces in the donor cornea or in the artificial tissue in such a way as to generate control data and transmit the latter to the first laser device or the further laser device with which a blank is generable, the blank being defined by a correction zone situated in the center of the blank, a transition zone arranged around said correction zone and an edge zone arranged around said transition zone, the edge zone being provided for the subsequent separation prior to an insertion of the lamella into the cornea of the eye, and this blank can be removed from the donor cornea or the artificial tissue and affixed on a holder for the purposes of processing with the second laser device.

In a second example variant, the planning device is configured to define cut surfaces in the donor cornea or the artificial tissue in such a way as to generate control data and transmit the latter to the first laser device or the further laser device with which a blank is generable, the blank being defined by a correction zone situated in the center of the blank and a transition zone arranged around said correction zone, and this blank can be processed further by the second laser device in the original donor cornea or in the artificial tissue.

In this second variant, it is also further advantageous for example if the planning device is configured to define cut surfaces in the donor cornea or the artificial tissue in such a way as to generate control data and transmit these to the first laser device or the further laser device with which a blank is generable, the latter moreover having an edge zone which is arranged around the transition zone and which is provided for subsequent separation prior to an insertion of the lamella into the cornea of the eye.

Typical dimensions of the corresponding zones are as follows:

for the diameter of the correction zone: 3 mm to 8 mm for the width of the transition zone (radial): at least 10 $\mu$m, for example between 50 $\mu$m and 2 mm for the width of the edge zone: 0 to 1 mm for the edge thickness: 1 $\mu$m to 50 $\mu$m. In this case, the edge thickness is the thickness to be obtained, especially in the outer ring-shaped 10 $\mu$m edge region of the lamella.

In this case, correction zone, transition zone and edge zone are generally circular or annular. However, depending on patient-specific conditions, an elliptical or irregular shape is also possible. The latter can also be used for the purposes of positioning the lamella in the cornea of the eye at the correct angle.

It should be observed here that there currently is no technology for generating a defined edge geometry in the case of a patient-specifically shaped lamella. The femtosecond laser cuts used in the experimental method for generating the approximately cylindrical blank (which strictly speaking describes a cap of a spherical shell) and the subsequent excimer laser processing to form a patient-specifically shaped lamella are not yet able to generate a precise edge geometry. Without the special measures described herein, the assumption can be made that for example the edge thickness alone deviates randomly by up to 30 $\mu$m or up to 100% from the target value. By way of example, an edge zone according to the invention for subsequent separation is also advantageous for these reasons.

The Zernike polynomials up to the 6th order which are used for the patient-specific adaptation by application of an excimer laser device as a second laser device represent a significant limitation of the method. Although there is a 10th order Zernike decomposition for an already existing topography-guided treatment using an excimer device, for example the MEL, this treatment method has not yet been applied ex vivo to date and is also not accessible to the procedure practiced until now. Thus, there currently is no other tested technology for controlling an excimer laser device during ex vivo processing of a lamella.

Although processing the cornea ex vivo using an excimer laser was already formulated as a goal towards the end of the 1980s and there has also already been a practical attempt at implementation (P. Homolka et al., Das Excimer Laser Corneal Shaping-(ELCS)System. Elektrotechnik and Informationstechnik, vol. 117, (2000)), this approach did not become established in clinical practice. The reason for this failure was firstly due to the still immature excimer laser technology and secondly also due to the lack of modern diagnostic capabilities such as high-resolution OCT equipment. Moreover, only mechanical microkeratomes were available for the generation of blanks and their processing accuracy was one order of magnitude lower than that of current femtosecond laser systems. Consequently, uncertainty about the precise initial shape of the processed donor cornea was also added to the roughness of the transplants of approximately 10 μm caused by the excimer technology. The lack of accuracy resultant therefrom prevented the practical application of the generated transplants.

A lamella with an edge thickness of at least 30 μm is currently used in sIALK. This is advantageous in view of the mechanical stability of the lamella and the ability to manipulate the latter, but leads to a ring-shaped cavity arising at the point of contact between stroma, lamella and cap despite the vacancy. Although a cavity is filled with the tissue fluid, it is unphysiological and should be avoided where possible. Thus, the prior art does not contain technology for generating a specific edge geometry of the lamella.

It is difficult to produce a precise geometry using an excimer laser device if the spatial frequencies are high in comparison with the beam diameter. The production of a simple cylindrical blank using a femtosecond laser device already shows that, in principle, there is the option of generating precise edges using a femtosecond laser device. Hence, a combination of processing steps using a femtosecond laser device as a pre-processing second laser device and an excimer laser device as post-processing second laser device is proposed, wherein however the processing principles, which are described here and which consequently should be planned appropriately and converted into control data, have to be taken into account.

The planning device according to the invention for generating control data for a treatment system for refractive surgery, in particular for keratoplasty, is for example configured in particular to generate the control data for the second laser device in such a way that a defined edge geometry is obtained in the patient-specifically shaped lamella, wherein the edge thickness is no more than 30 μm, for example between 5 μm and 15 μm, in the case of a pocket cut where no vacancy is generated for this reason, or the edge thickness of the lamella is adapted to the vacancy geometry where a corneal volume is removed and hence a vacancy is generated.

It is for example further configured to determine a substantially ring-shaped transition zone at the edge of the lamella, within which the edge thickness gradually transitions into a patient-specific thickness profile, and the control data are generated in such a way that there is no processing of the edge of the lamella by the second laser device.

The edge of the lamella should therefore essentially already be generated according to the specifications during the generation of the blank for example by application of a femtosecond laser device as the pre-processing first or further laser device, while the actual processing/individualization of the lamella prior to the implantation in a recipient's eye is implemented for example by application of an excimer laser device as post-processing second laser device.

When viewed in the axial direction, the implant according to the invention has a for example a round central correction zone. In this zone, said implant is shaped such it achieves the sought-after correction, for example of a thickness profile of the cornea or a topography or a wavefront, to the best possible extent. The correction zone is surrounded by a ring-shaped transition zone which serves to obtain a continuous transition of the shape at the edge of the correction zone to the edge zone. This likewise ring-shaped zone extends to the outer edge of the implant with a height (thickness) that is as constant as possible. Naturally, this edge zone may also be omitted, but this also removes the advantage connected therewith. This is because the purpose of the edge zone is, where possible, to avoid or at least reduce the effect of a centration error during the sequential laser processing on the outer edge thickness of the implant. A further purpose of an (extensive) edge zone consists of protecting the closer edge zone of an (almost finished) lamella until the implantation of the latter, as will be explained below.

It should be observed that the measures relating to a defined edge of the lamella and a temperature regime are particularly effective if the equipment coordinate systems of the first laser device, of the characterization device and of the second laser device are coupled to one another by use of a registration by way of the planning device and if the supplied second measurement data of the lamella are uniquely registrable to the equipment coordinate systems. However, even without such coupling and registration to one another, the measures relating to a defined edge of the lamella and a temperature regime during the processing contribute to an improved precision in relation to the prior art and, in particular, to a restoration of a normal corneal geometry with an improved optical function of the cornea in relation to the prior art.

As already described, a ring-shaped transition zone is provided at the edge, the radial width of said transition zone being at least 10 μm, for example between 50 μm and 2 mm, and in another example between 50 μm and 500 μm. The edge thickness is gradually converted into the patient-specific thickness profile within this transition zone. In the simplest case, this is implemented by a linear connection of the edge thickness of D(r=r_max, Phi) to D(r=r_max. edge thickness, Phi). Further configurations are obvious to a person skilled in the art, smoothing in Phi is also possible.

The edge thickness and the profile within the transition zone is for example obtained by the interaction of a femtosecond laser device as a pre-processing first or further laser device and an excimer laser device as a post-processing second laser device. In particular, the excimer processing is carried out in such a way in a variant of the invention that there is no excimer ablation at the edge of the blank. Firstly, the excimer laser device should be prevented from changing the edge thickness which was precisely generated using the femtosecond laser device and, secondly, a blank holder must not be ablated should the blank be affixed on said holder for processing by the excimer laser device, as this could contaminate the lamella. To further improve this aspect, the transition zone in a variant of the invention is wholly or partly generated by the femtosecond laser device as pre-processing first or further laser device, for example by virtue of a conical basic geometry of the edge zone of the blank being generated.

Currently, control of an excimer laser device during the ex vivo processing of a lamella is carried out with a shot pattern which decomposes the Zernike expansion of the difference profile into individual ablation volumes. Currently, this expansion is only implemented up to the 6th order of the polynomial. However, the expansion beyond the 6th order is advantageous in these ex vivo processing instances in order to be able to generate finer structures. However, it is not mandatory to carry out such an expansion. Instead, the difference profile can be directly decomposed into individual ablation volumes (shot decomposition). In any case, it is crucial to carry out the processing so that the temperature of the blank does not exceed 40° C. To this end, the shot distribution and the laser frequency of the scanning spot laser are adapted accordingly.

Furthermore, the following should be observed in relation to the prior art, its problems and the measures according to the invention resulting therefrom:

The improvement in the corrected visual acuity (CDVA) connected with the regularization of the corneal thickness is already a good result for the patient. To obtain a good uncorrected visual acuity (UCVA), there is in principle also the option of carrying out a refractive corrective treatment, but photorefractive keratectomy (PRK) would always be connected with the loss of the Bowman's membrane, which is a medically questionable option in the case of a biomechanically unstable eye. Laser in-situ keratomileusis (LASIK) is out of the question on account of the even greater biomechanical implication and a femtosecond lenticule extraction (small incision lenticule extraction, SMILE) treatment would hardly be able to be carried out from the surgical point of view. An anterior chamber lens would be conceivable but represents a high risk for such a patient; the same applies to an intraocular lens (IOL), which would replace a non-cloudy lens in this case (clear lens exchange).

If only the regularization of the corneal thickness (pachymetry) is sought after, a state is obtained in which the patient's eye has good visual acuity with a visual aid (spectacles, contact lens). Additional measures are required if an even better state is sought after, for example so that good visual acuity can be obtained without a correction by way of spectacles. The main features for solving this problem are already formulated in part in DE 10 2007 019 815 A1 or WO 2008/131888 A1, but specific or even advantageous configurations are not known to date.

Therefore, an example planning device is configured to produce the control data for the second laser device such that a refractive power and/or an astigmatism is impressed on the blank.

For a more precise interplay between the second laser device and the first or further laser device used to prepare the blank, a further example planning device according to the invention is configured to define the position of calibration marks in the transition zone and/or edge zone and to generate control data for the first laser device or the further laser device, by application of which control data these calibration marks are able to be introduced during processing with the first laser device or the further laser device, with the calibration marks being defined such that they are usable as a single or multiple orientation tools during a processing of the blank by application of the second laser device.

In particular, it is helpful if the planning device according to the invention defines the calibration marks so that these are arranged multiple times above one another and/or offset from one another and/or at different levels in the blank to be processed by the second laser device.

Thus, the introduction of calibration cuts is possible in each case as an optional step according to the invention when cutting the blank in the donor cornea or in the artificial tissue, for example by application of a femtosecond laser device, calibration cuts in an excavation volume additionally described below being particularly advantageous in this case.

Then, it is possible in each case to interrupt the processing as a further optional step when processing using an ablating excimer laser device for example as a second laser device, followed by the option of continuing after a visual inspection by the user. In this context, the user in particular checks whether one or more of the calibration marks have already been struck by the excimer treatment, and makes a corresponding decision about whether to continue the removal. This method can also be implemented in automated fashion by application of an appropriate image recording and image processing apparatus, this automation being implemented by a controller with appropriate software.

In general, the processing with the ablating excimer laser can be implemented in various phases, for example a first phase for removing the epithelium and a second phase for processing the stromal tissue.

Specifically, the calibration marks are for example introduced into the excavation volume, as shown in some exemplary embodiments. If this is carried out in one work step with the generation of the other cut surface, for example using a femtosecond laser device as a first or further laser device, these calibration marks can be positioned very accurately in relation to the other cut surfaces. An accuracy better than 1 µm is achievable both axially and laterally. If the excimer removal then reaches such a calibration mark when processing the blank using for example an excimer laser device as a second laser device, the calibration mark being maintained for some time in the tissue as a gas bubble-filled cut surface, then this exhibits a very characteristic change in the optical appearance of the respective calibration mark. An optimal overlay of the two laser processing activities can be obtained in this manner by a geometric design of calibration marks and ablation profile, which design is within the capabilities of a person skilled in the art, in particular in the excavation volume, as a result of which it is possible for example to generate a precise edge thickness with little outlay.

As already indicated, it is furthermore advantageous for example if a planning device is configured to define a processing profile for the second laser device and determine the control data in such a way that the profile of the correction zone situated in the center of the blank and of the transition zone arranged around said correction zone is generable by application of the second laser device and an excavation is generable in the edge zone arranged around this transition zone, for the removal of a lamella carved out of the donor cornea or the artificial tissue, or for further processing of the blank on a holder, in such a way that the holder cannot be hit by a processing laser beam of the second laser device.

Generating an excavation within the method for producing the implant in the form of a patient-specific lamella is an important part of the invention. Excavation refers to the creation of a usually ring-shaped cavity around the external periphery of the implant. This trench-like cavity serves to aid the surgeon with exposing the implant within the scope of its separation, or with sparingly removing non-required material from the periphery of the implant in the case of an already exposed implant. This prevents damage to the extremely fine edge structure of the material prior to the insertion of the lamella into a corresponding cut surface or structure in the cornea of the recipient's eye. A few characteristic features of an excavation are further illustrated in the drawings of the exemplary embodiments.

In this case, typical values for the width of an excavation (radial) are: 500 µm to 3 mm. In this case, the diameter of an optionally performed additional excavation cut should be at least 100 µm greater than the diameter of the actual implant, that is to say the final lamella. To provide a real order of magnitude, it should likewise be mentioned in this context that calibration cuts are generated in one to one hundred surfaces for the purposes of generating the above-described calibration marks.

Moreover, it is advantageous for example if the planning device according to the invention is configured to generate the control data taking into account a defined initial hydration state of the blank or of the lamella ex vivo, and to take account of the change in the hydration state of the lamella during or after the implementation, for example by application of a constant expansion factor.

The problem of different hydration levels is already known within the scope of corneal transplants and is reduced by a specific treatment of the transplants. However, this arises for the first time in this form in the context of sIALK because corneas were not previously shaped ex vivo in patient-specific fashion by application of an excimer laser device, for example. In addition to swelling and shrinking, the removal efficiency of the excimer laser device is also changed in this case by the hydration.

It was conspicuous in the analysis of the previous procedure that the variability of the material, in particular its state of hydration, may be the source of significant errors. This was not clear to date and requires suitable measures for ultimately being able to predict the geometry of the lamella in the recipient's cornea, in particular its thickness, more precisely.

An additional option for improved control of the hydration state lies in the use of artificial tissue material with well-defined parameters, from which the lamella to be implanted can then be carved in more controlled fashion by application of the second laser device—as a replacement for natural transplant material.

Moreover, the blank or the lamella could be stained with a dye for better handling, said dye steadily disappearing following the implantation of the lamella.

The object is furthermore achieved by a treatment system according to the invention for refractive surgery, in particular for keratoplasty, comprising a first laser device for generating at least one cut surface in a cornea of an eye, for example a femtosecond laser device, a second laser device for processing a blank to form the patient-specifically shaped lamella, for example an excimer laser device, at least one characterization device, for example an OCT device, and a planning device according to the invention described herein.

A treatment system according to the invention comprising a further laser device for generating or pre-processing the blank, for example a femtosecond laser device, is advantageous.

In a particular configuration of the treatment system according to the invention, the second laser device contains a holder for affixing the blank during the processing.

A particular configuration of the treatment system according to the invention comprises a temperature control device, for example such that the temperature of the blank can be lowered in such a way that the blank is able to be processed in the frozen state.

Then, the blank can be cooled for the purposes of processing of the blank. During the processing, the reduction in temperature leads to more precise processing as a result of reducing the drying up and/or reducing temperature-dependent material changes. This is particularly important when processing is implemented with a high laser frequency and much energy is accordingly introduced quickly into the blank. This energy input is not always restricted to the immediate interaction zone between laser radiation and material, but may also comprise the surroundings of the interaction zone as a result of heat transfer and heat conduction. Since (artificial) materials generated by biotechnology in particular sometimes react sensitively to an increase in temperature, that is to say exhibit disadvantageous changes, cooling of the blank may provide a remedy in an embodiment of both the treatment system according to the invention and a method according to the invention.

In an example configuration, the temperature of the blank, in particular of a blank affixed to a holder for processing purposes, is reduced in this case to approximately the dew point of the surroundings. By way of example, this means that a surface temperature of approximately 9° C. is set in the case of an air temperature of 20° C. and 50% humidity.

In a further example configuration, the temperature of the blank on the holder is reduced so far that it freezes. Such a reduction in the temperature of the blank under its freezing point can also be obtained in normal ambient air surroundings by way of an appropriately cold holder. The laser processing is then implemented on the frozen blank. By way of example, the temperature of the blank can be reduced to below 0° C., below −5° C. or below −10° C. An advantage of the very low temperature consists in the fact that the interaction of the laser radiation with non-ablated material is reduced. Thawing or frosting of the material is minimized by way of a fast process (e.g., all of the laser processing is carried out within 1 minute) or compensated by an appropriately designed ablation process.

In a specific treatment system according to the invention, the temperature control device thereof has at least one of the following configurations:

active electrical cooling by application of a Peltier element, active cooling by application of an introduced coolant, active cooling by an air flow, passive cooling by pre-cooling the holder with or without the blank affixed thereon, a chamber, separated from the surroundings, for processing the blank.

Thus, the holder may be equipped with a cooling mechanism for cooling purposes. By way of example, this is active electrical cooling by application of a Peltier element. However, active cooling by use of an introduced coolant (e.g., nitrogen, glycerol, ethanol) or passive pre-cooling in a correspondingly cold environment (refrigerator) is also conceivable. Cooling can be subject to closed-loop control, with the temperature of the holder or the temperature of the blank being monitored in the case of an appropriate embodiment of the holder.

Instead of being subject to normal ambient air (23° C., 50% relative humidity), the blank can also be impinged by an air current which also influences the temperature of the blank in addition to the usual effect of removing debris. This is implemented by adjusting the temperature and/or humidity. Alternatively, a protective gas can be used instead of ambient air. For further improvement of this method, the blank may be processed in a chamber that has been separated from the surroundings.

As a guideline for specific processing of the blank on a holder in the second laser device, in particular an excimer laser device, work can be carried out with the following values:

the temperature the holder should be approximately 1° C. to 20° C. for a frost-free operation.

the temperature the holder should be approximately –30° C. to –1° C. for a "frost operation".

A treatment system according to the invention which comprises a device for monitoring the temperature of the blank and/or of the holder while the blank is processed is further advantageous.

The object is also achieved by a planning method according to the invention, which realizes the generation of control data for a treatment system for refractive surgery, in particular for keratoplasty, in accordance with a coding of the described planning device.

Not least, the object of the invention is achieved by a method for refractive surgery, in particular keratoplasty, in which at least one cut surface is generated in the cornea of an eye, a lamella for insertion into the cornea of a (recipient's) eye is planned with the aid of the planning method, generated with the aid of the generated control data and inserted into the at least one cut surface, optionally also into a vacancy that has arisen by the cut surface formation, in the cornea of the eye.

Thereby, one of the method variants outlined below can be resorted to when producing the lamella.

Variant 1:
1. Cutting the blank in a donor cornea or an artificial tissue by application of a first or further laser device, in particular a femtosecond laser device (also referred to as fs laser keratome).
2. Processing the blank in the donor cornea or the artificial tissue using a second laser device, in particular an excimer laser device, in the process generating a correction zone, a transition zone and an edge zone, and optionally introducing an excavation for exposing the implant (that is to say the almost finished lamella).
3. Resecting the implant from the donor cornea or the artificial tissue.

Variant 2:
1. Cutting the blank in a donor cornea or an artificial tissue by application of a first or further laser device, for example a femtosecond laser device.
2. Resecting the blank from the donor cornea or the artificial tissue and positioning said blank on a holder.
3. Processing the blank on the holder using a second laser device, in particular an excimer laser device, in the process generating the correction zone, the transition zone and the edge zone, and optionally introducing an excavation.
4. Optional: Separating the implant (that is to say ultimately the patient-specific lamella) from the remains of the blank.

Variant 3:
1. Positioning the blank (from a donor cornea material or an artificial tissue material) on a holder.
2. Optional: Starting the cooling of the holder.
3. Processing the blank on the holder using a second laser device, in particular an excimer laser device, and optionally using a first or further laser device, in particular a femtosecond laser device (fs laser keratome), in the process generating the correction zone, the transition zone and the edge zone. Introducing an excavation.
4. Optional: Separating the implant from the holder after the holder has been heated.

Variant 4:
1. Carrying out one of variants 1 to 3.
2. Separating the implant from the holder.
3. Flipping the implant (a spherical shell-shaped volume can be flipped).
4. Positioning the implant on the holder, with the previous top side now being located at the bottom.
5. Carrying out one of variants 1 to 3 again.

BRIEF DESCRIPTION OF THE DRAWINGS

The present invention will now be explained on the basis of example embodiments. In the drawings.

DETAILED DESCRIPTION

Figure 1A:
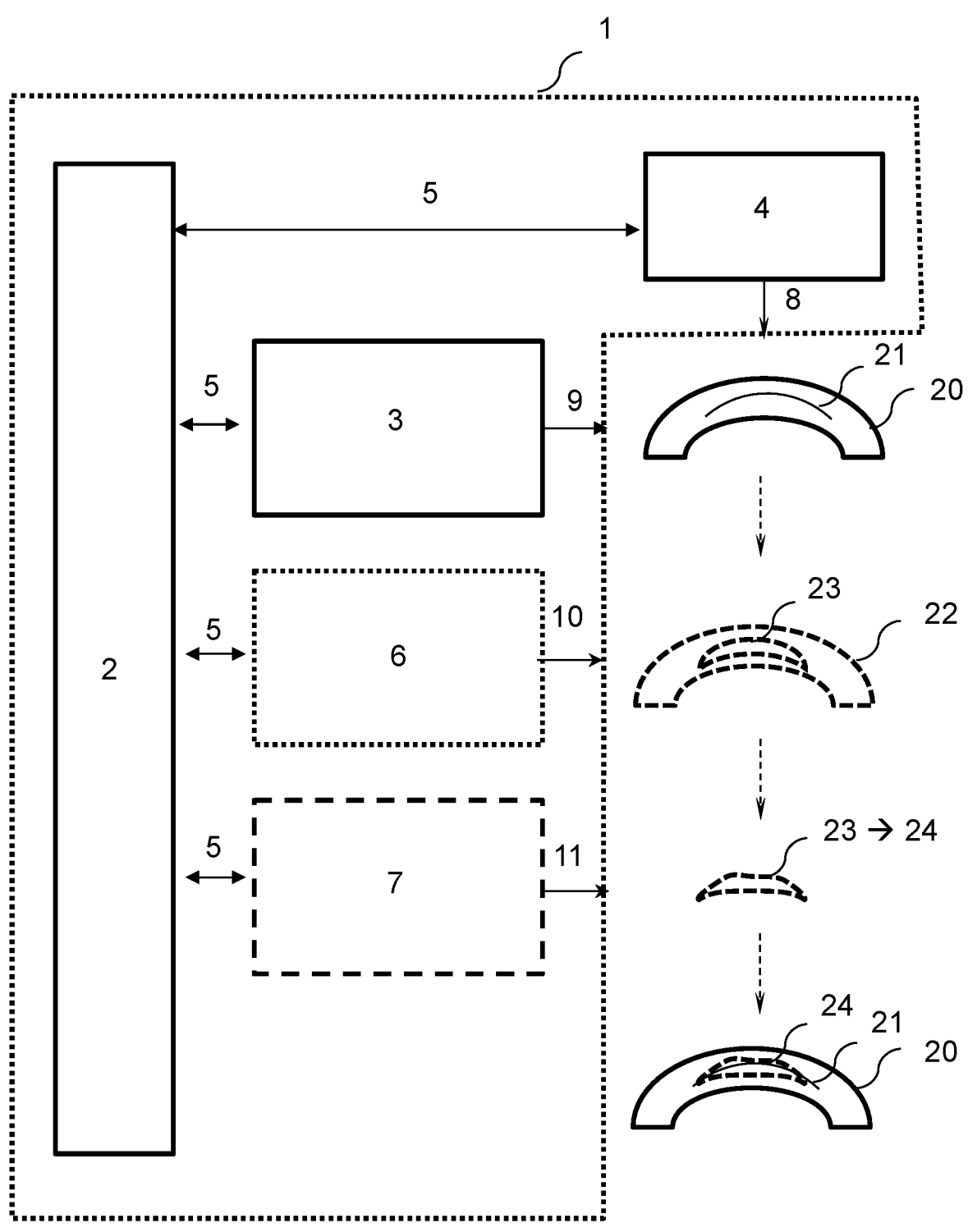
FIG. 1a is a diagram of an example first treatment system according to the invention with a first planning device according to the invention, which does not reflect the exact physical conditions.
Figure 1B:
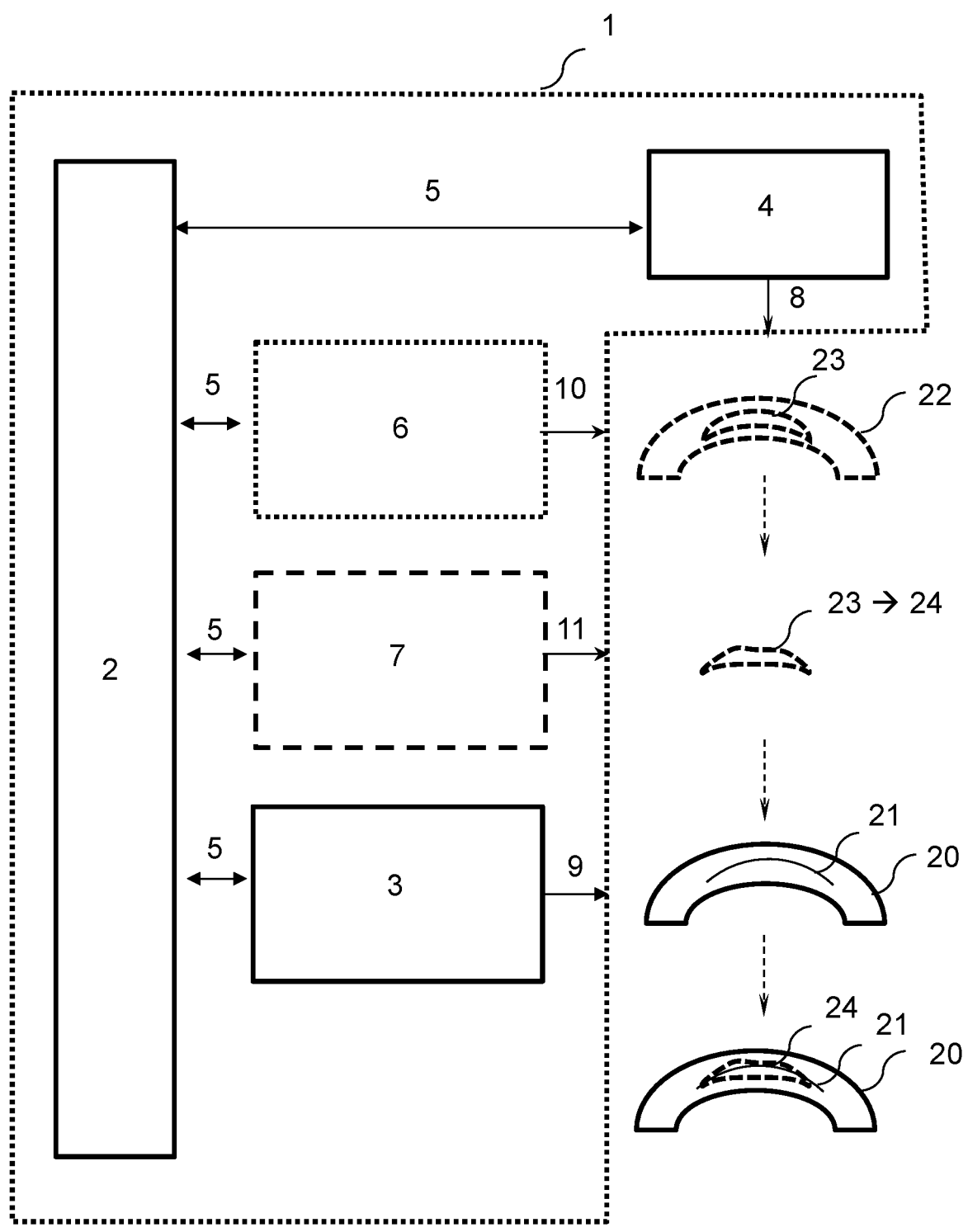
FIG. 1b is a diagram of an example second treatment system according to the invention with a second planning device according to the invention.
Figure 1C:
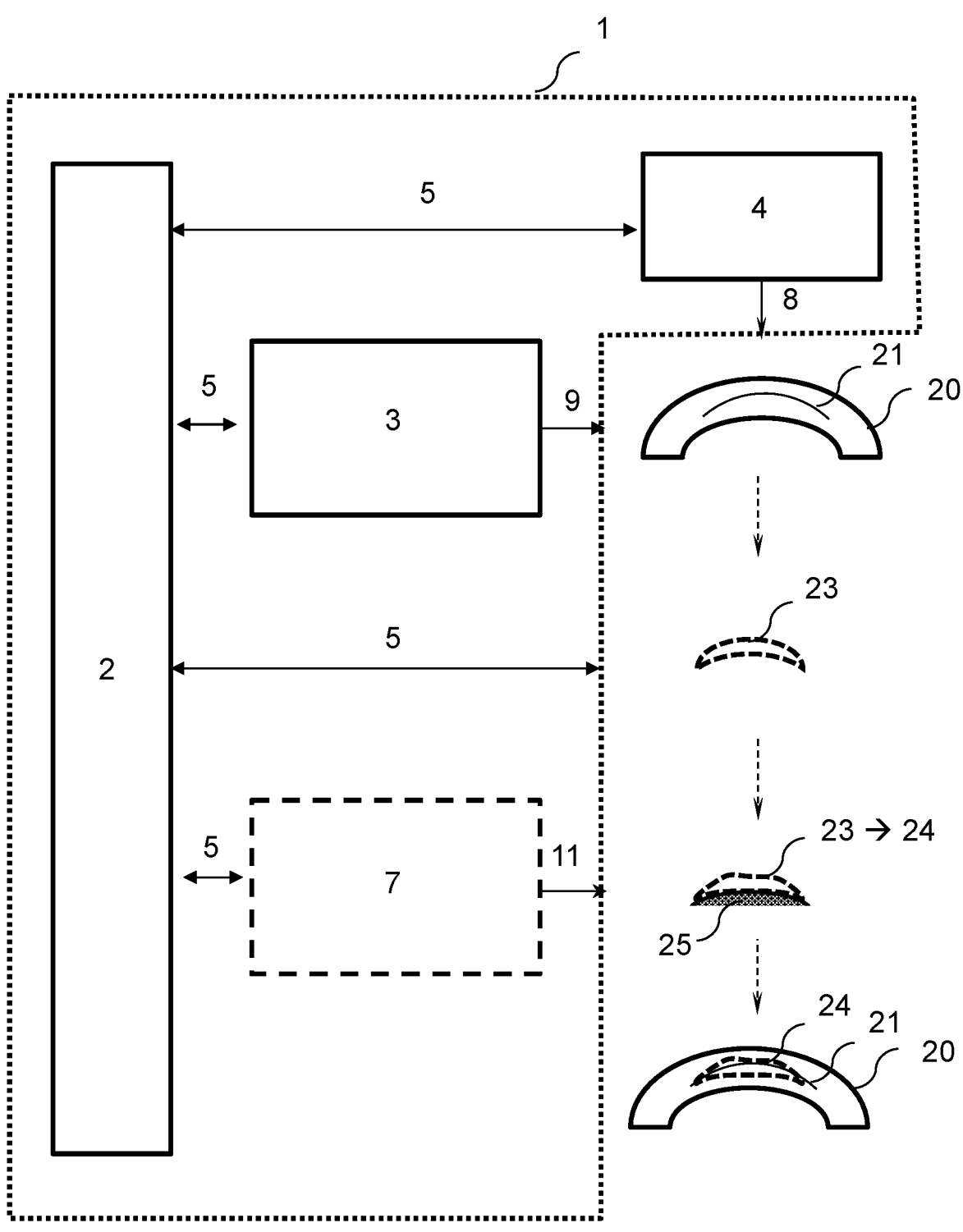
FIG. 1c is a diagram of an example third treatment system according to the invention with a third planning device according to the invention.

In each of FIGS. 1a to 1c, the treatment system 1 comprises a planning device 2, a characterization device 4, which is configured to generate measurement data relating to parameters of the cornea 20 of an eye using examination radiation 8, a first laser device 3, which is a femtosecond laser device in this case and which is configured to generate a vacancy or, as illustrated here, a pocket cut 21 in the cornea 20 of a recipient's eye by application of a focused femtosecond laser beam 9 (the direction of incidence of the beam is not illustrated here—however, a person skilled in the art knows the optical setup of corresponding devices).

All characterization and laser devices of the treatment system 1 contain interfaces 5 to the planning device 2.

FIGS. 1a and 1b furthermore comprise a pretreating further laser device 6, which is likewise a femtosecond laser device, with the first femtosecond laser device 3 and the pretreating further femtosecond laser device being able to be one and the same device or else two different laser devices. The pretreating further laser device cuts a blank 23 from the cornea of a donor eye 22 using a focused femtosecond laser beam 10. FIGS. a to 1c furthermore comprises a post-treating second laser device, in this case an excimer laser device 7, which carves the lamella 24 to be implanted from the blank 23 using excimer laser radiation 11, said lamella then ultimately being implanted in the pocket 21 of the cornea of the recipient's eye 20.

The planning device 2 is configured to couple the equipment coordinate systems of the involved laser devices 3, 6, 7 and characterization devices 4 by use of a registration and to uniquely register the supplied measurement data of the lamella 23 to be implanted to the equipment coordinate systems.

While the pocket cut 21 is initially generated in the cornea of the recipient's eye 20 in FIG. 1a, and the blank 23 is only subsequently generated in the donor eye and removed from the latter in order to subsequently be formed into the lamella 24 as intended to be handled, the blank 23 is initially processed in full to form the lamella 24 in FIG. 1b. Only then is a pocket cut 21 implemented in the cornea of the recipient's eye 20 for the purposes of preparing the implantation.

In FIG. 1c, in turn, work is carried out using standardized blanks 23 (for example made of an artificial tissue material), which are then only still post-processed to form the lamella 24. However, this also shows the affixment of the blank 23 to a holder 25 while being processed by application of the excimer laser device 7 as second laser device. The holder is cooled while the blank is processed.

FIGS. 2a to 2f show various processing stages and processing variants of a blank 23 in a donor cornea or an artificial tissue for a procedure for generating an implant/a patient-specific lamella 24 as is obtainable, for example, with the aid of the planning device 2 according to the invention—for the basic variant of processing the blank 23 within the donor cornea or the artificial tissue to the point where the patient-specific lamella 24 is generated.

Figures 2A, 2B, 2C, 2D, 2E, 2F:
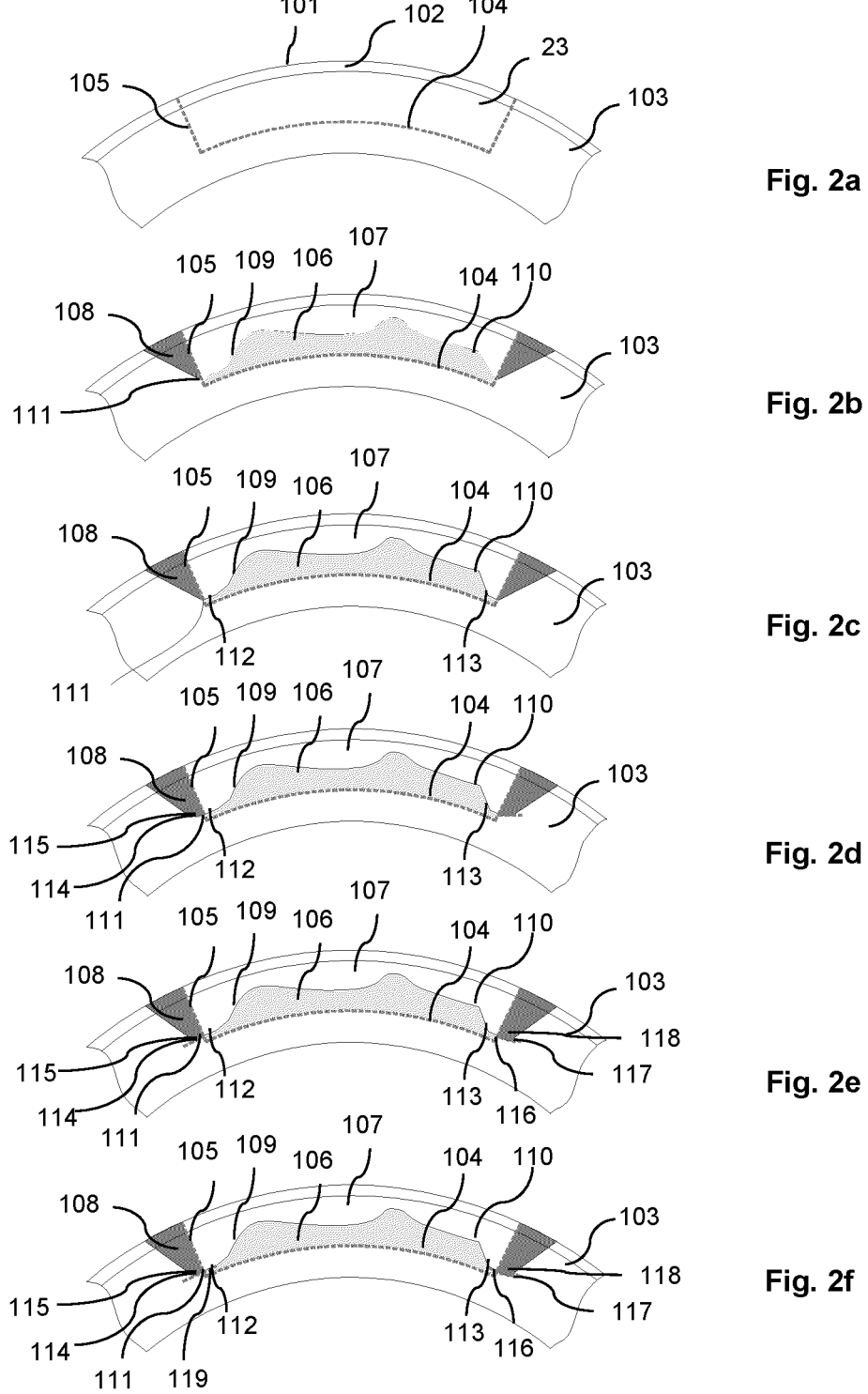
FIGS. 2a to 2f depict various processing stages and processing variants of a blank in a donor cornea or an artificial tissue for a procedure for generating an implant/a patient-specific lamella as is obtainable, for example, with the aid of the planning device according to the invention for the basic variant of processing the blank within the donor cornea or the artificial tissue up to the point where the patient-specific lamella is fully generated.

In this case, FIG. 2a represents a donor cornea with its individual layers, the epithelium layer 101, the Bowman's membrane 102 and the corneal stroma 103. Moreover, the cuts that fundamentally separate the blank 23 from the donor cornea are shown: The lamellar cut 104 and the side cut 105.

FIG. 2b moreover represents the implant 106, to be generated, in the form of the patient-specific lamella 24 and, following therefrom, the ablation volume 107 intended to be ablated using the second laser device 7. Also shown is the excavation 108 intended to subsequently serve the simplified separation of the implant 106 from the donor cornea (or an artificial tissue). Moreover, also visible in FIG. 2b are the two outer boundaries of the correction zone 109, 110, and the upper outer boundary of the implant 111, which represents the intersection of side cut 105 and final implant top side.

In addition to the regions, cuts and markings specified in FIGS. 2a and 2b, FIG. 2c represents the outer boundary of the transition zone 112, 113.

In addition to the regions, cuts and markings already specified in FIGS. 2a to 2c, FIG. 2d shows calibration marks 114. With the aid thereof, it is then for example possible to modify the shape of the excavation 108 in relation to the shape 115 of the excavation shown in FIGS. 2b and 2c. By introducing calibration marks 114 by application of the first 3 or further laser device 6 (that is to say the femtosecond laser device in this case), the removal profile in the edge regions is subsequently controlled during the ablation process by application of the second laser device 7 (in this case the excimer laser device).

In addition to the aforementioned calibration marks 114, FIG. 2e shows further calibration marks: Calibration marks above the implant in its edge region 116 and calibration marks next to the implant, and stacked calibration marks 117, 118.

Additionally, a side cut 119 is planned with the first 3 or further laser device 6, the femtosecond laser device, in FIG. 2f, said side cut hence defining the height of the implant 106 in its edge zone, in particular of the patient-specific lamella 24 as final product of planning and processing the blank 23, more reliably than if this height is generated only by application of the ablation by way of the second laser device 7, the excimer laser device.

Thus, the patient-specific lamella 24 is carved from a blank 23 in the donor cornea in these variants of FIGS. 2a to 2f. The implant 106 is only removed from this donor cornea or the artificial tissue following this processing.

FIGS. 3a to 3f show various processing stages and processing variants of a blank 23 in an artificial tissue or a donor cornea for a procedure for generating an implant/a patient-specific lamella 24 as is obtainable, for example, with the aid of the planning device 2 according to the invention—for the basic variant of further processing the blank by application of the second laser device 7, in this case an excimer laser device, in such a way that the blank 23 is taken from the artificial tissue and affixed on a holder 25. This is the preferred way, especially when processing artificial tissue, since a reliable temperature regime should be ensured in the case of an affixment on a holder 25 during the processing with the second laser device 7, that is to say an excimer laser device. In this respect, artificial tissue is even more sensitive than the natural tissue of a donor cornea.

Figures 3A, 3B, 3C, 3D, 3E, 3F:
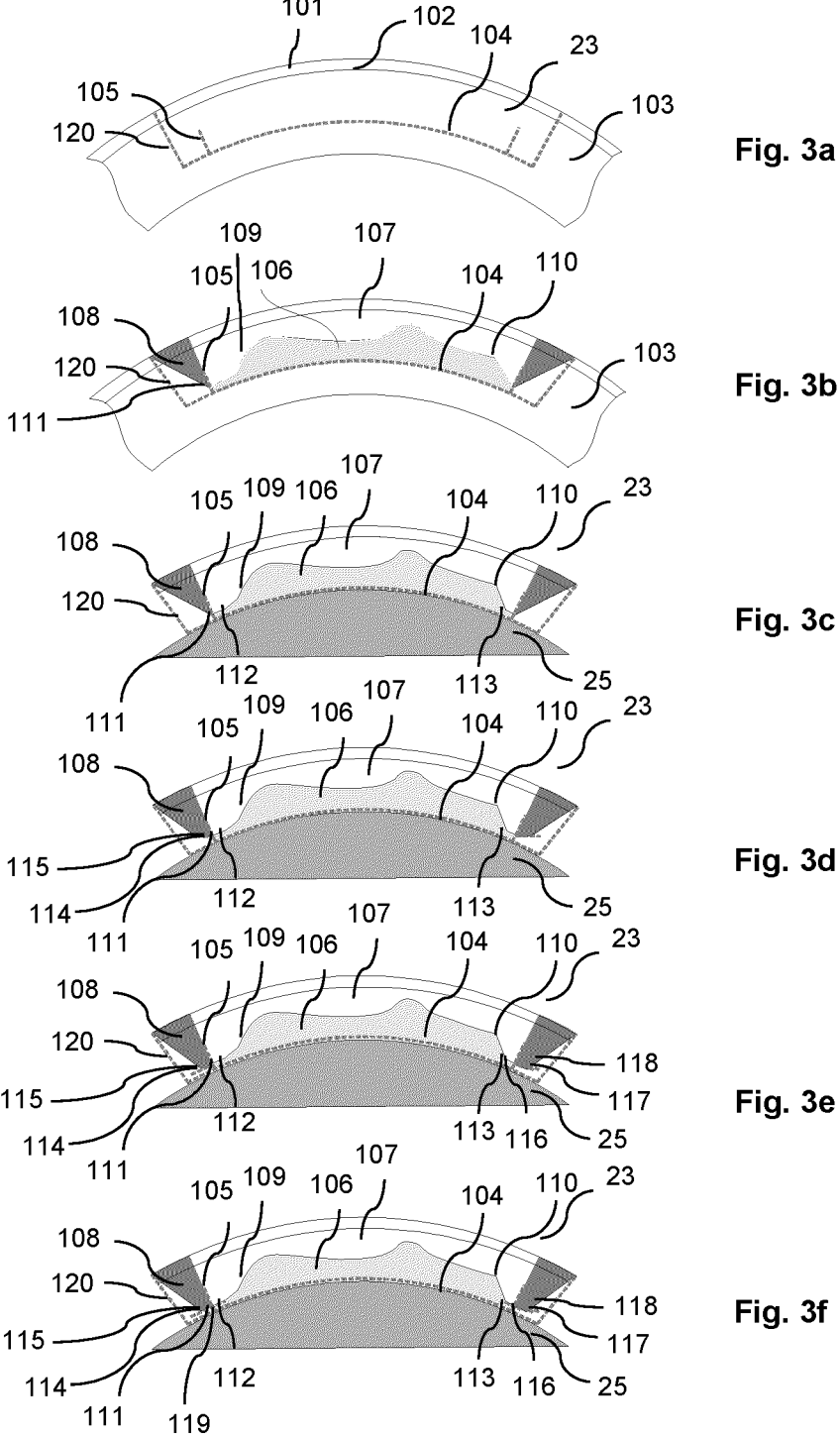
FIGS. 3a to 3f depict various processing stages and processing variants of a blank in a donor cornea or an artificial tissue for a procedure for generating an implant/a patient-specific lamella as is obtainable, for example, with the aid of the planning device according to the invention for the basic variant of further processing the blank by application of the second laser device, in this case an excimer laser device, in such a way that the blank is taken from the donor cornea or the artificial tissue and affixed on a holder.

In this case, FIG. 3a initially represents an artificial tissue which virtually "reproduces" a natural cornea, with epithelium layer 101, Bowman's membrane 102 and corneal stroma 103. Moreover, the cuts that fundamentally separate the blank 23 from the artificial tissue are shown: The lamellar cut 104 and the side cut 105, which in this case is not guided from the lamellar cut 104 up to the epithelium layer 101, but only guided into the stromal layer. However, the blank 23 is only really separated from the artificial tissue by the modified side cut 120.

In addition to the regions, cuts and markings already specified in FIG. 3a, FIG. 3b also represents the implant 106 to be generated, in the form of the personalized lamella, and, following therefrom, the ablation volume 107 and an excavation 108: It is evident from the representation of the excavation 108 in particular that the modified side cut 120 is planned so that the excavation 108 is completely comprised in the blank 23 separated from the artificial tissue by the cuts. Moreover, once again, also visible in FIG. 3b are the two outer boundaries of the correction zone 109, 110, and the upper outer boundary of the implant 111, which represents the intersection of side cut 105 and final implant top side.

In FIG. 3c, the blank 23 has firstly been taken from the artificial tissue and has been affixed to a holder 25. In addition to the regions, cuts and markings specified in FIGS. 3a and 3b, the outer boundary of the transition zone 112, 113 is also represented here.

In addition to the regions, cuts and markings already specified in FIGS. 3a to 3c, FIG. 3d in turn shows calibration marks 114. In this case, too, the shape 115 of the excavation 108 can be influenced with the aid of the calibration marks 114.

In addition to the aforementioned calibration marks 114, FIG. 3e shows further calibration marks: Calibration marks above the implant in its edge region 116 and calibration marks next to the implant 106, and stacked calibration marks 117, 118—all of these in more or less the same way as when processing the blank 23 to form a patient-specific lamella 24 in the donor cornea. However, this variant allows a temperature regime when processing the blank 23 with the second laser device 7, the excimer laser device, to be introduced and maintained very precisely from the moment the blank 23 is affixed to the holder 25.

Additionally, a side cut 119 is planned with the first 3 or further 6 laser device, the femtosecond laser device, in FIG. 3f, said side cut hence reliably defining the height of the implant 106 in its edge zone, in particular of the patient-specific lamella 24 as final product of planning and processing the blank 23.

Figures 4A, 4B, 4C:
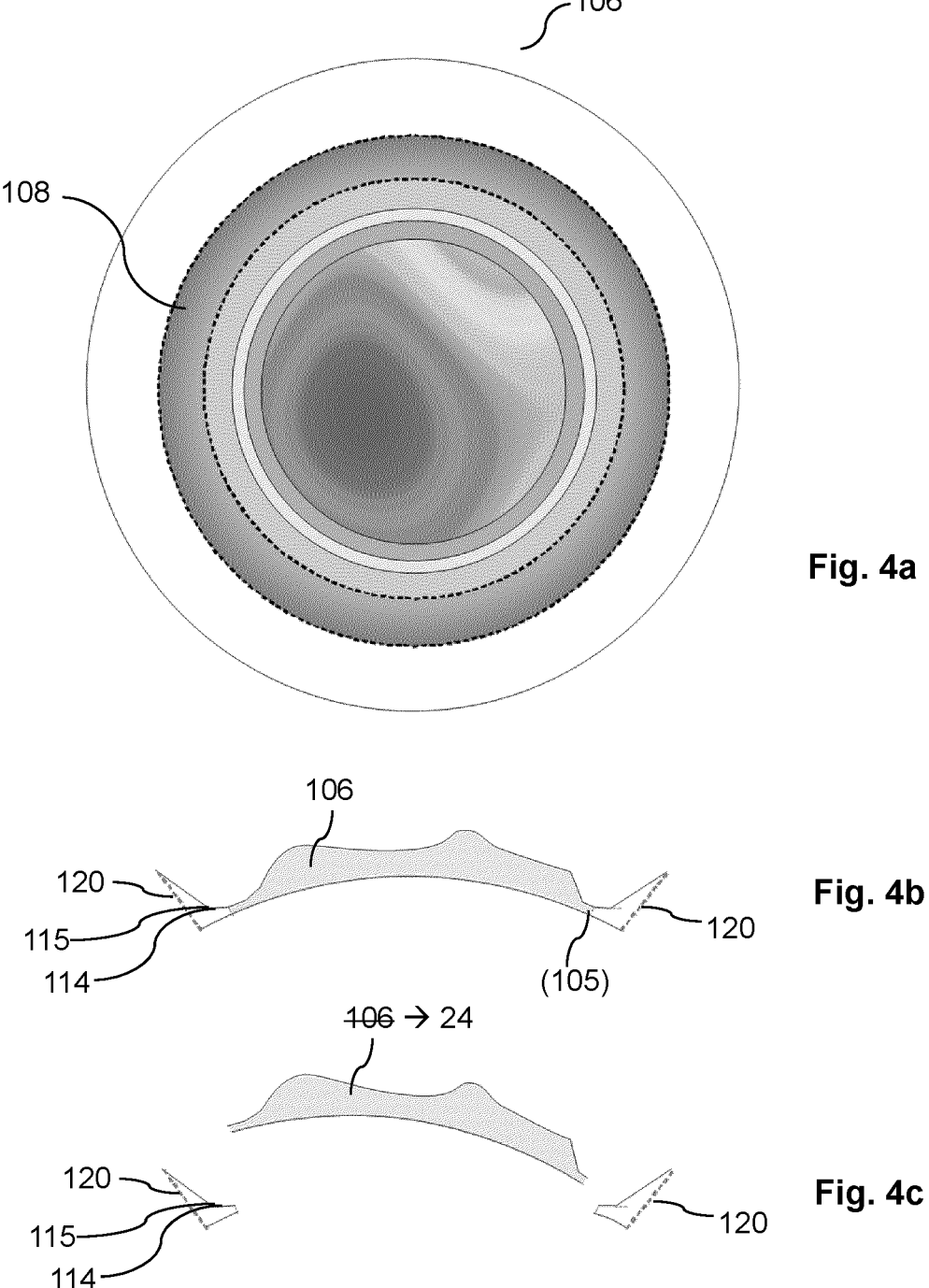
FIGS. 4a to 4c depict an implant following the processing with the laser devices of the treatment system according to the invention and before its insertion into a cut surface of the cornea in a recipient's eye.

FIGS. 4a to 4c finally show an implant 106 following the processing with the laser devices 3, 7, 6 of the treatment system 1 according to the invention and before its insertion into a cut surface 21 of the cornea in a recipient's eye.

FIG. 4a represents such an implant 106, the blank 23 of which was processed on a holder 25 using the second laser device 7, the excimer laser device, in a plan view, while FIGS. 4b and 4c show the same implant 106 in a side view. The actual edge of the lamella 24 to be implanted was precisely carved out by way of the excavation. However, it is protected until after the processing thereof using the second laser device 7. The separation point for finally removing this extended "protective edge" was already created by the side cut of the blank 23 at the start of the entire production process for the patient-specific lamella 24. This patient-specific lamella 24 then remains following the actual separation of the "protective edge", as shown in FIG. 4c, and can be inserted into the prepared cut surface 21 or structure in the cornea 20 of the recipient's eye.

The aforementioned features of the invention, which are explained in various exemplary embodiments, can be used not only in the combinations specified in an exemplary manner but also in other combinations or on their own, without departing from the scope of the present invention.

A description of a piece of equipment relating to method features is analogously applicable to the corresponding method with respect to these features, while method features correspondingly represent functional features of the equipment described.

The invention claimed is:

1. A treatment system for refractive surgery, including for keratoplasty, said treatment system comprising:
   a planning device that generates control data for the treatment system for the refractive surgery;
   a first laser device and at least one characterization device;
   a second laser device;
   wherein the first laser device, is configured to generate at least one incision within a corneal stroma of an eye and is controllable by operation of the control data to generate the at least one incision within the corneal stroma thereby to create at least one cut surface defining an intrastromal pocket in the stroma, the intrastromal pocket being bounded by the corneal stroma and having an anterior surface and a posterior surface and a perimeter within the corneal stroma;
   the planning device including a first interface that supplies first measurement data regarding parameters of the cornea to the characterization device,
   a second interface that supplies second measurement data or model data about a lamella which is insertable into the intrastromal pocket following the generation of the at least one cut surface
   wherein the second laser device is configured to process a blank to form the lamella and comprises a holder on which the blank is affixable during the treatment by the second laser device;
   wherein the planning device is furthermore configured to generate control data for the second laser device of the treatment system, to control the second laser to process the blank to form the lamella to be shaped in a patient-specific fashion, and wherein the planning device further comprises a fourth interface that transmits control data to the second laser device;
   wherein the first laser device, the second laser device and the characterization device each have an equipment coordinate system, and the first laser device, the second laser device and the characterization device are coupled or couplable with respect to one another by a registration of the equipment coordinate systems, and the supplied second measurement data or model data of the lamella are registrable with respect to the equipment coordinate systems; and
   wherein the planning device further generates control data that facilitates active cooling of the holder, active cooling of the blank in the holder itself or both.

2. The treatment system as claimed in claim 1, wherein the first laser device, comprises a femtosecond laser device.

3. The treatment system as claimed in claim 1, wherein the characterization device, comprises an OCT (optical coherence tomography) device.

4. The treatment system as claimed in claim 1, wherein second laser device of the treatment system, comprises an excimer laser device.

5. The treatment system as claimed in claim 1, wherein the planning device is further configured to generate control data to institute a temperature regime that maintains a temperature below a maximum temperature for processing the blank to form the lamella using the second laser device.

6. The treatment system as claimed in claim 1, wherein the planning device is further configured to determine a substantially ring-shaped transition zone at an edge of the lamella, within which an edge thickness gradually transitions to a patient-specific thickness profile, and furthermore wherein control data are generated such that there is no processing of the edge of the lamella by the second laser device.

7. The treatment system as claimed in claim 1, wherein the planning device is furthermore configured to generate control data for the first laser device or a third laser device, an equipment coordinate system of which is likewise coupled to the aforementioned equipment coordinate systems by application of a registration, to generate or pre-process the blank, wherein the blank is able to be generated from a natural donor cornea or from artificial tissue, or the blank is pre-processable therein, by generating one or more cut surfaces in the donor cornea or the artificial tissue by operation of the first laser device or the third laser device.

8. The treatment system as claimed in claim 7, wherein the third laser device, comprises a further femtosecond laser device.

9. The treatment system as claimed in claim 7, wherein the planning device is further configured to define the one or more cut surfaces in the donor cornea or in the artificial tissue in such a way as to generate control data and transmit the control data to the first laser device or the third laser device with which a blank is generatable, the blank being defined by a correction zone situated in a center of the blank, a transition zone arranged around said correction zone and an edge zone arranged around said transition zone, the edge zone being provided for the subsequent separation prior to an insertion of the lamella into the cornea of the eye, and wherein the blank can be removed and affixed on a holder for purposes of processing with the second laser device.

10. The treatment system as claimed in claim 9, wherein the planning device is configured to define a position of calibration marks in the transition zone and/or edge zone and to generate control data for the first laser device or the third laser device, by application of which control data these calibration marks are able to be introduced during processing with the first laser device or the third laser device, wherein the calibration marks are defined such that they are usable as a single or multiple orientation feature during a processing of the blank by operation of the second laser device.

11. The treatment system as claimed in claim 7, wherein the planning device is configured to define the one or more cut surfaces in the donor cornea or the artificial tissue in such a way as to generate control data and transmit the control data to the first laser device or the third laser device with which a blank is generatable, the blank being defined by a correction zone situated in the center of the blank and a transition zone arranged around said correction zone, and this blank is further processable by the second laser device in the original donor cornea or in the artificial tissue.

12. The treatment system as claimed in claim 11, wherein the planning device is further configured to define the one or more cut surfaces in the donor cornea or the artificial tissue in such a way as to generate control data and transmit the control data to the first laser device or the third laser device with which a blank is generatable, the blank further having an edge zone which is arranged around the transition zone and which is provided for subsequent separation prior to an insertion of the lamella into the cornea of the eye.

13. The treatment system as claimed in claim 12, wherein the planning device is configured to define a processing profile of a correction zone for the second laser device and determine the control data in such a way that the processing profile of the correction zone situated in a center of the blank and of the transition zone arranged around said correction zone is generatable by operation of the second laser device and an excavation is generatable in the edge zone arranged around the transition zone, thereby facilitating removal of a lamella carved out of the donor cornea or the artificial tissue, or thereby facilitating further processing of the blank on a holder, in such a way that the holder cannot be hit by a processing laser beam of the second laser device.

14. The treatment system as claimed in claim 11, wherein the planning device is configured to define a position of calibration marks in the transition zone and/or edge zone and to generate control data for the first laser device or the third laser device, by application of which control data these calibration marks are able to be introduced during processing with the first laser device or the third laser device, wherein the calibration marks are defined such that they are usable as a single or multiple orientation feature during a processing of the blank by operation of the second laser device.

15. The treatment system as claimed in claim 14, wherein the planning device is further configured to define calibration marks which are arranged multiple times above one another and/or offset from one another and/or at different levels in the blank to be processed by the second laser device.

16. The treatment system as claimed in claim 1, wherein the planning device is configured to generate the control data taking into account a defined initial hydration state of the blank or of the lamella ex vivo, and a change in the hydration state of the lamella during or after the implementation.

17. The treatment system as claimed in claim 16, wherein the planning device is configured to generate the control data taking into account the defined initial hydration state of the blank or of the lamella ex vivo, and the change in the hydration state of the lamella during or after the implementation, by application of a constant expansion factor.

18. The treatment system as claimed in claim 1, wherein the planning device further generates control data that facilitates active cooling of the holder, the blank or both such that a temperature of the blank can be lowered in such a way that the blank is processed in a frozen state or wherein the planning device further generates control data that facilitates active cooling of the holder, the blank or both such that the temperature is lowered to a dewpoint of air in an airstream so that constant humidity is maintained thereby balancing condensation and evaporation of the blank.

19. The treatment system as claimed in claim 1, further comprising a temperature control device which comprises at least one of the following configurations:

active electrical cooling by application of a Peltier element;

active cooling by application of an introduced coolant;

active cooling by an air flow;

passive cooling by pre-cooling the holder with or without the blank affixed thereon; and a chamber, separated from surroundings, for processing the blank.

20. The treatment system as claimed in claim 1, further comprising a temperature sensor that monitors the temperature of the blank and/or of the holder during the processing.

* * * * *